United States Patent [19]

Chin

[11] 4,400,203
[45] Aug. 23, 1983

[54] SUBSTITUTED AMINO CARBOXYETHYL HALOACETAMIDE HERBICIDE ANTIDOTES

[75] Inventor: Hsiao-Ling M. Chin, Walnut Creek, Calif.

[73] Assignee: Stauffer Chemical Company, Westport, Conn.

[21] Appl. No.: 220,925

[22] Filed: Dec. 29, 1980

[51] Int. Cl.³ .............................................. A01N 25/32
[52] U.S. Cl. ....................................... 71/100; 71/103; 71/106; 71/111; 560/24; 560/25
[58] Field of Search .................. 71/100, 103, 111, 106

[56] References Cited

U.S. PATENT DOCUMENTS 4,276,078 6/1981 Pallos et al. ............................ 71/100
4,297,295 10/1981 Gaughan ................................ 71/100

Primary Examiner—Catherine L. Mills
Attorney, Agent, or Firm—Leona L. Lauder; Beth Kovitz

[57] ABSTRACT

Herbicide antidote compounds having the formula

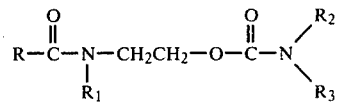

in which

R is halomethyl wherein halo refers to chlorine, bromine or iodine and the methyl group is mono- or di-substituted;

$R_1$ is selected from the group consisting of alkyl having 1-4 carbon atoms, inclusive; phenyl, and methylaminocarboxyethyl;

$R_2$ is selected from the group consisting of hydrogen and methyl, and, $R_3$ is selected from the group consisting of alkyl having 1-4 carbon atoms, inclusive; p-toluenesulfonyl; p-chlorophenylsulfonyl; halophenyl wherein halo refers to a member of the group consisting of chlorine, bromine and iodine and wherein said phenyl group may be mono-, di-, or tri-halosubstituted on the same or different substituents; and, halomethylphenyl wherein halo refers to a member of the group consisting of fluorine, chlorine, bromine and iodine and said methyl group may be mono-, di-, or tri-substituted.

6 Claims, No Drawings

SUBSTITUTED AMINO CARBOXYETHYL HALOACETAMIDE HERBICIDE ANTIDOTES

FIELD OF THE INVENTION

This invention relates to herbicide antidotes, and, more particularly, to certain substituted amino carboxyethyl haloacetamides which are useful as herbicide antidotes.

BACKGROUND OF THE INVENTION

Herbicides are generally used to control or eradicate weed pests. They have gained a high degree of commercial success because it has been shown that such control can increase crop yield and reduce harvesting costs.

The most popular methods of herbicide application include: pre-plant incorporation into the soil; in-furrow application to seeds and surrounding soil; pre-emergence surface treatment of seeded soil; and post-emergence treatment of the plant and soil.

A manufacturer of an herbicide generally recommends a range of application rates and concentrates calculated to maximize weed control. The range of rates varies from approximately 0.01 to 50 pounds per acre (0.0111 to 56 kilograms per hectare (k/ha)), and is usually in the range of from 0.1 to 25 pounds per acre (0.112 to 28 k/ha). The term "herbicidally effective amount" describes an amount of an herbicide compound which controls or modifies plant growth. The actual amount used depends upon several considerations, including particular weed susceptibility and overall cost limitations.

The most important factor influencing the usefulness of a given herbicide is its selectivity towards crops. In some cases, a beneficial crop is susceptible to the effects of the herbicide. In addition, certain herbicidal compounds are phytotoxic to some weed species but not to others. To be effective, an herbicide must cause minimal damage (preferably no damage) to the beneficial crop while maximizing damage to weed species which plague that crop.

To preserve the beneficial aspects of herbicide use and to minimize crop damage, many herbicide antidotes have been prepared. These antidotes reduce or eliminate damage to the crop without substantially impairing the damaging effect of the herbicide on weed species. See, for example, U.S. Pat. Nos. 4,021,224 and 4,021,229 and Belgian Pat. No. 846,894.

The precise mechanism by which an antidote reduces herbicidal crop injury has not been established. An antidote compound may be a remedy, interferent, protectant, or antagonist. As used herein, "antidote" describes a compound which has the effect of establishing herbicide selectivity, i.e., continued herbicidal phytotoxicity to weed species and reduced or non-phytotoxicity to cultivated crop species. The term "antidotally effective amount" describes an amount of an antidote compound which counteracts a phytotoxic response of a beneficial crop to an herbicide.

Thiocarbamate herbicides are particularly effective in the control of grassy type weeds which interfere with the cultivation of a wide variety of crops, e.g., barley, corn, lentils, peanuts, peas, potatoes, soybeans, spinach, tobacco and tomatoes. Frequently the effective use of these herbicides requires the addition of an antidote compound.

DESCRIPTION OF THE INVENTION

It has now been discovered that certain substituted amino carboxyethyl haloacetamides are effective antidotes for the protection of a variety of crops from thiocarbamate herbicide injuries. Such compounds have the following formula:

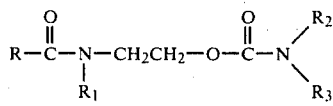

in which
R is halomethyl wherein halo refers to chlorine, bromine or iodine and the methyl group is mono- or di-substituted;

$R_1$ is selected from the group consisting of alkyl having 1-4 carbon atoms, inclusive; phenyl, and methylaminocarboxyethyl;

$R_2$ is selected from the group consisting of hydrogen and methyl, and, $R_3$ is selected from the group consisting of alkyl having 1-4 carbon atoms, inclusive; p-toluenesulfonyl; p-chlorophenylsulfonyl; halophenyl wherein halo refers to a member of the group consisting of chlorine, bromine and iodine and wherein said phenyl group may be mono-, di-, or tri-halosubstituted on the same or different substituents; and, halomethylphenyl wherein halo refers to a member of the group consisting of fluorine, chlorine, bromine and iodine and said methyl group may be mono-, di-, or tri-substituted.

This invention also embodies a two-part herbicidal system comprised of (a) an herbicidally effective amount of a thiocarbamate compound of the formula

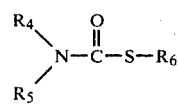

in which
$R_4$ is alkyl having 1-6 carbon atoms, inclusive;
$R_5$ is selected from the group consisting of alkyl having 1-6 carbon atoms, inclusive; and cyclohexyl; or
$R_4$ and $R_5$ form indistinguishable parts of a single alkylene ring having 4-10 carbon atoms, inclusive; and
$R_6$ is selected from the group consisting of alkyl having 1-6 carbon atoms, inclusive; haloalkyl wherein halo is selected from the group consisting of chlorine, bromine and iodine and alkyl has 1-6 carbon atoms, inclusive; alkenyl having 2-6 carbon atoms, inclusive; halo alkenyl wherein halo is selected from the group consisting of chlorine, bromine and iodine and alkenyl has 2-6 carbon atoms, inclusive; benzyl; and halo-substituted benzyl, wherein halo is selected from the group consisting of chlorine, bromine and iodine; and (b) a non-phytotoxic antidotally effective amount of a compound of the formula $$\underset{\underset{R_1}{|}}{R-\overset{\overset{O}{\|}}{C}-N}-CH_2CH_2-O-\overset{\overset{O}{\|}}{C}-N\diagdown_{R_3}^{R_2}$$

in which
- R is halomethyl wherein halo refers to chlorine, bromine or iodine and the methyl group is mono- or di-substituted;
- $R_1$ is selected from the group consisting of alkyl having 1-4 carbon atoms, inclusive; phenyl, and methylaminocarboxyethyl;
- $R_2$ is selected from the group consisting of hydrogen and methyl, and,
- $R_3$ is selected from the group consisting of alkyl having 1-4 carbon atoms, inclusive; p-toluenesulfonyl; p-chlorophenylsulfonyl; halophenyl wherein halo refers to a member of the group consisting of chlorine, bromine and iodine and wherein said phenyl group may be mono-, di-, or tri-halosubstituted on the same or different substituents; and, halomethylphenyl wherein halo refers to a member of the group consisting of fluorine, chlorine, bromine and iodine and said methyl group may be mono-, di-, or tri-substituted.

By way of exemplification, the active thiocarbamate herbicides employed in the invention may include the following: S-ethyl dipropyl thiocarbamate, S-ethyl diisobutyl thiocarbamate, S-propyl dipropyl thiocarbamate, S-propyl butylethylthiocarbamate, S-(2,3,3-trichloroallyl)diisopropyl thiocarbamate, S-ethyl N-ethyl N-cyclohexyl thiocarbamate, S-ethyl hexahydro-1H-azepine-1-carbothioate, isopropyl-1-hexahydro-1,4-azepine-1-carbothioate, S-benzyl N,N-disec-butylthiolcarbamate, S-(4-chlorobenzyl) N,N-diethyl thiolcarbamate and combinations thereof.

This invention also includes the method of establishing herbicidal selectivity which comprises applying to the locus where protection is desired an antidotally effective amount of a compound of the formula $$\underset{\underset{R_1}{|}}{R-\overset{\overset{O}{\|}}{C}-N}-CH_2CH_2-O-\overset{\overset{O}{\|}}{C}-N\diagdown_{R_3}^{R_2}$$

in which
- R is halomethyl wherein halo refers to chlorine, bromine or iodine and the methyl group is mono- or di-substituted;
- $R_1$ is selected from the group consisting of alkyl having 1-4 carbon atoms, inclusive; phenyl, and methylaminocarboxyethyl;
- $R_2$ is selected from the group consisting of hydrogen and methyl, and,
- $R_3$ is selected from the group consisting of alkyl having 1-4 carbon atoms, inclusive; p-toluenesulfonyl; p-chlorophenylsulfonyl; halophenyl wherein halo refers to a member of the group consisting of chlorine, bromine and iodine and wherein said phenyl group may be mono-, di-, or tri-halosubstituted on the same or different substituents; and, halomethylphenyl wherein halo refers to a member of the group consisting of fluorine, chlorine, bromine and iodine and said methyl group may be mono-, di-, or tri-substituted.

The locus where selectivity is desired may include soil, seeds, seedlings and vegetation.

Preparation

The thiocarbamates of the present composition are either commercially available or can be prepared by the procedures described in U.S. Pat. Nos. 2,913,327, 2,983,747, 3,133,947 3,185,720 and 3,198,786.

The substituted amino carboxyethyl haloacetamides of this invention can be prepared according to the following general procedure, depending upon the starting materials. An N-β-hydroxyethylamide is reacted with an appropriate isocyanate in suitable solvent. Examples of suitable solvents include tetrahydrofuran, dichloromethane, benzene and methylbenzene. The reaction is catalyzed using, for example, triethylamine and dibutyl tin dilaurate. After refluxing, the solvent may be removed. Structure may be confirmed using nuclear magnetic resonance (NMR) spectroscopy.

In an alternative procedure, at least some of the compounds of this invention may be prepared by use of an N-β-oxyethylamide salt as an intermediate. The salt is prepared by reacting an appropriate N-β-hydroxyethylamide with sodium hydride in a suitable solvent. Tetrahydrofuran is an example of a suitable solvent. The reaction mixture is refluxed, cooled and then allowed to stand in an ice bath.

The N-β-oxyethylamide salt is then reacted with an appropriate N,N-disubstituted-N-halocarbonyl amine. No catalyst is added. After refluxing, the solvent is removed. Structure may be confirmed using NMR spectroscopy.

The following examples illustrate the preparation of specific compounds according to this general method. (Compound numbers correspond to those in Tables I, IV and V.)

EXAMPLE I (Compound No. 1)

Preparation of N-β-methylaminocarboxyethyl-N-methyl-chloroacetamide

Seven and fifty-seven hundreths grams (g) (0.05 mole) of N-methyl-N-hydroxyethyl chloroacetamide and 4.27 g of methyl isocyanate were dissolved in 150 milliliters (ml) of dichloromethane. Five drops each of dibutyl tin dilaurate and triethylamine were added. The reaction mixture was refluxed for 5 hours, cooled and vacuum stripped. The yield was 10.86 g of N-β-methylaminocarboxyethyl-N-methyl chloroacetamide. ($n_D^{30}=1.4906$) Structure was confirmed using NMR.

EXAMPLE II (Compound No. 2)

Preparation of N-β-methylaminocarboxyethyl-N-methyl dichloroacetamide

Three and three tenths g (0.017 mole) of N-methyl-N-hydroxyethyl dichloroacetamide were dissolved in 100 ml tetrahydrofuran. One and forty-five hundreths g (0.025 mole) of methylisocyanate were added, followed by 3 drops each of triethylamine and dibutyl tin dilaurate. The reaction mixture was refluxed for three hours. The solvent was removed using a Rinco evaporator and an oil pump. The yield was 4.26 g of N-β-methylaminocarboxyethyl-N-methyldichloroacetamide. ($n_D^{30}$=1.4976). Structure was confirmed using NMR.

EXAMPLE III (Compound No. 6)

Preparation of
N-β-dimethylaminocarboxyethyl-N-methyl dicloroacetamide

This is an example of a compound prepared using an N,-β-oxyethylamide salt.

Two and seventy-nine hundreths grams (0.015 mole) of N-methyl-N-hydroxethyl dichloroacetamide were dissolved in 120 ml of tetrahydrofuran. One-half g sodium hydride was added and the reaction mixture was refluxed for 2 hours. The mixture was cooled and allowed to stand in an ice bath.

One and sixty-one hundreths grams of dimethyl carbamyl chloride were added dropwise to the mixture containing the N-β-oxyethyl amide salt. During the period of addition, the mixture was stirred and the ice bath was allowed to melt. The mixture was stirred overnight, then refluxed for 2 hours, cooled and stripped. The N-β-dimethylaminocarboxyethyl-N-methylchloroacetamide was taken up in dichloromethane, washed, dried and stripped. Yield was 3.21 g ($n_D^{30}$=1.4910) Structure was confirmed by NMR.

EXAMPLE IV (Compound No. 14)

Preparation of
N-β-p-methylphenylsulfonylcarbamyloxyethyl-N-methyl dichloroacetamide Two and seventy-four hundreths g (0.0147 mole) of N-methyl-N-hydroxyethyl dichloroacetamide and 2.91 g (0.0147 mole) of p-toluenesulfonyl isocyanate were dissolved in 110 ml of benzene. Three drops each of dibutyl tin dilaurate and triethylamine were added. The reaction mixture was refluxed for 3 hours, cooled, Rinco stripped and oil pump stripped. Yield was 5.45 g of N-β-p-methylphenylsulfonylcarbamyloxyethyl-N-methyl dichloroacetamide. ($n_D^{30}$=1.5371) Structure was confirmed using NMR.

The compounds prepared according to these procedures appear in Table I.

TABLE I

SUBSTITUTED AMINOCARBOXYETHYL HALOACETAMIDES $$R-\overset{O}{\underset{\|}{C}}-\underset{R_1}{N}-CH_2CH_2-O-\overset{O}{\underset{\|}{C}}-N\overset{R_2}{\underset{R_3}{\diagup\diagdown}}$$

| Cmpd. No. | R | $R_1$ | $R_2$ | $R_3$ | Chemical Name | Physical Constant |
|---|---|---|---|---|---|---|
| 1 | ClCH$_2$ | CH$_3$ | H | CH$_3$ | N—β-methylaminocarboxyethyl-N—methyl chloroacetamide | $n_D^{30}$ = 1.4906 (impure) |
| 2 | Cl$_2$CH | CH$_3$ | H | CH$_3$ | N—β-methylaminocarboxyethyl-N—methyl dichloroacetamide | $n_D^{30}$ = 1.4976 |
| 3 | BrCH$_2$ | CH$_3$ | H | CH$_3$ | N—β-methylaminocarboxyethyl-N—methyl bromoacetamide | $n_D^{30}$ = 1.5112 |
| 4 | Cl$_2$CH | C$_2$H$_5$ | H | CH$_3$ | N—β-methylaminocarboxyethyl-N—ethyl dichloroacetamide | $n_D^{30}$ = 1.4952 |
| 5 | ClCH$_2$ | CH$_2$CH$_2$OC(O)—NHCH$_3$ | H | CH$_3$ | N,N—di-(methylaminocarboxyethyl)chloroacetamide | $n_D^{30}$ = 1.500 |
| 6 | Cl$_2$CH | CH$_3$ | CH$_3$ | CH$_3$ | N—β-dimethylaminocarboxyethyl-N—methyl dichloroacetamide | $n_D^{30}$ = 1.4910 |
| 7 | ClCH$_2$ | 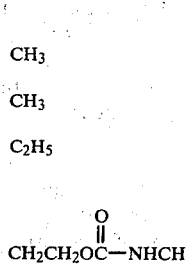 | H | CH$_3$ | N—β-methylaminocarboxyethyl-N—phenyl chloroacetamide | $n_D^{30}$ = 1.5356 |
| 8 | Cl$_2$CH |  | H | CH$_3$ | N—β-methylaminocarboxyethyl-N—phenyl dichloroacetamide | m.p. = 70–75° C. |
| 9 | ClCH$_2$ | CH$_3$ | H |  | N—β-3,4-dichlorophenylaminocarboxyethyl-N—methyl chloroacetamide | m.p. = 137–139° C. |
| 10 | ClCH$_2$ | CH$_3$ | H | 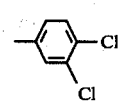 | β-m-trifluoromethylphenylcarbamyloxyethyl-N—methyl chloroacetamide | $n_D^{30}$ = 1.5023 |
| 11 | Cl$_2$CH | CH$_3$ | H | 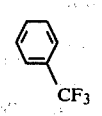 | N—β-m-trifluoromethylphenylcarbamyloxyethyl-N—methyl dichloroacetamide | $n_D^{30}$ = 1.5056 |

TABLE I-continued
SUBSTITUTED AMINOCARBOXYETHYL HALOACETAMIDES

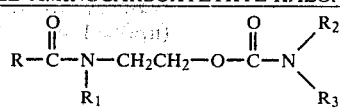

$$\begin{array}{ccc} & O & & & O & R_2 \\ & \| & & & \| & / \\ R-C-N-CH_2CH_2-O-C-N \\ & | & & & & \backslash \\ & R_1 & & & & R_3 \end{array}$$

| Cmpd. No. | R | $R_1$ | $R_2$ | $R_3$ | Chemical Name | Physical Constant |
|---|---|---|---|---|---|---|
| 12 | $BrCH_2$ | $CH_3$ | H | (phenyl)-$CF_3$ | N—β-m-trifluoromethylphenylcarbamyloxyethyl-N—methyl bromoacetamide | $n_D^{30} =$ 1.5178 |
| 13 | $ClCH_2$ | $CH_3$ | H | $SO_2$-(phenyl)-$CH_3$ | N—β-p-methylphenylsulfonyl carbamyloxy-ethyl-N—methyl chloroacetamide | m.p. = 127–131° C. |
| 14 | $Cl_2CH$ | $CH_3$ | H | $SO_2$-(phenyl)-$CH_3$ | N—β-p-methylphenylsulfonylcarbamyloxy-ethyl-N—methyl dichloroacetamide | $n_D^{30} =$ 1.5371 |
| 15 | $BrCH_2$ | $CH_3$ | H | $SO_2$-(phenyl)-$Cl$ | N—β-p-chlorophenylsulfonylcarbamyloxyethyl-N—methyl bromoacetamide | $n_D^{30} =$ 1.5293 |

Testing

Stock solutions of the herbicides were prepared by diluting the requisite amount of each herbicide in water. Examples of solution compositions and application rates are summarized in Table II.

TABLE II

| | Herbicide Stock Solutions | | | |
|---|---|---|---|---|
| | Composition | | Application | |
| Herbicide Name | Herbicide (mg)* | Water (ml) | ml/flat** | lb/acre |
| VERNAM ® 6E S—propyl-N,N— dipropyl thio-carbamate | 533 3000 | 400 500 | 5 5 | 1.25 6.00 |
| EPTAM ® 6E S—ethyl-N,N— dipropyl thiocarbamate | 2225 | 350 | 5 | 6.00 |

*The weight is measured in terms of mg of formulated herbicide. The formulations used contained about 72% active herbicide compound.
**The flats measure 5.95 inches by 9.5 inches. Approximately four (4) mg/flat is equal to one (1) lb/acre.

In each case, the herbicide was incorporated into the soil prior to planting. In some cases the herbicide was incorporated into the soil alone in preparation for in-furrow application of the antidote; in others the herbicide solution was tank-mixed with the antidote solution prior to incorporation.

Stock solutions of each antidote compound were prepared at the desired concentrations by diluting the requisite amounts of each antidote in acetone. Examples of solution compositions, rates and application methods are summarized in Table III.

TABLE III

| Antidote Stock Solutions | | | | |
|---|---|---|---|---|
| Antidote: Substituted Amino Carboxyethyl Haloacetanilides | | | | |
| Composition | | Application | | |
| Antidote (mg) | Acetone (ml) | ml/flat | lb/acre | Method |
| 95 | 15 | 1.50 | 5.00 | IF* |
| 60 | 15 | 5.00 | 5.00 | PPI* |

*IF = In-furrow surface application of antidote.
**PPI = Pre-plant incorporation of tank-mixed solution of herbicide and antidote The antidote solutions were applied to the soil either by in-furrow surface application or by pre-plant incorporation. In all cases of pre-plant incorporation, the antidote was tank-mixed with the herbicide prior to incorporation into the soil.

For in-furrow application, a one pint (473 cubic centimeter (cc)) sample of soil containing the previously incorporated herbicide was removed and retained from each planting flat. After leveling and furrowing the soil, seeds of the crop or weed species were planted ½ inch deep (1.27 centimeter). Each flat was divided in half by a wooden barrier. A stock solution of the antidote was atomized directly onto the exposed seeds and soil in the open furrow on one side of the barrier. The seeds in the entire flat were then covered with the previously removed soil. The antidotally untreated sections of flats were compared for observed differences which would indicate lateral movement of the antidote through the soil.

Control flats contained crops treated with herbicide only.

All flats were placed on greenhouse benches where temperature was maintained between 70° and 90° F. (21.1° to 32.2° C.). The flats were watered by sprinkling as needed to assure good plant growth.

All of the soil used in the tests described herein was loamy sand soil treated with 50 parts per million (ppm) each of a commercially available fungicide, N-[(trichloromethyl)-thio]-4-cyclohexene-1,2-dicarboximide, and 18-18-18 fertilizer, which contains 18% by weight equivalent each of nitrogen, phosphorus pentoxide, and potassium oxide.

Injury ratings were taken four weeks after application of the antidote. The effectiveness of the antidote was determined by visual comparison of crop injury which occurred in the test flats to that which occurred in the control flats.

The treated crops initially screened for diminution of herbicidal injury were milo, wheat, cotton, rice, barley, corn and soybeans. Compounds which showed substantial activity were tested further. The herbicides and the most active antidote compositions were then screened on weed species. The weed species tested included watergrass (*Echinochloa crusgalli*), foxtail (*Setaria viridis*), and shattercane (*Sorghum bicolor*).

KEY TO TABLES IV AND V

Compound numbers in these tables correspond to the numbers and their chemical description in Table I. Compounds omitted in Table V were not tested on weed species.

Herbicides

VERNAM ®—S-propyl-N,N-dipropyl thiocarbamate
EPTAM ®—S-ethyl-N,N-dipropyl thiocarbamate

Antidotes

Application:
  IF = In-furrow surface application of antidote (soil previously treated with herbicide only)
  PPI = Pre-plant incorporation of tank-mixed solution of herbicide and antidote If no antidote was applied, the word "none" appears in the Antidote Rate column. These are the control flats for each crop. The results shown on this line are the percent injuries sustained by each of the crops when treated with the herbicide only at the rate specified.

All rates shown, for both herbicide and antidote, are in pounds per acre.

Injury Ratings

The injury to the crop (Table IV) or weeds (Table V) is shown as a percentage of damage done to the plants as compared to an evaluation of the undamaged state of the plants. The damage done to the plants is a function of the number of plants injured and the extent of injury to each plant. This rating is made four (4) weeks after application of the herbicide alone or of the herbicide in combination with the antidote.

An asterisk (*) in Table IV indicates that the antidote compound is active in reducing herbicidal injury to the crop. Parentheses around a number indicate that the test has been run more than once and the results are inconclusive.

Table V shows that the antidote compounds tested have no effect on weeds, i.e., herbicidal injury to the weeds is sustained even in the presence of an antidote compound.

TABLE IV

| Cmpd. No. | Herbicide | Rate | Antidote Rate | Method | Milo % Inj | Wheat % Inj | Cotton % Inj | Rice % Inj | Barley % Inj | Corn % Inj | Soybean % Injury |
|---|---|---|---|---|---|---|---|---|---|---|---|
| 1 | VERNAM | 1.25 | none | — | 100 | 95 | 60 | 100 | 90 | | |
|   | VERNAM | 1.25 | 5.00 | IF | 100 | *80 | 60 | 100 | 90 | | |
|   | VERNAM | 6.00 | none | — | | | | | | 90 | 60 |
|   | VERNAM | 6.00 | 5.00 | IF | | | | | | 90 | 100 |
|   | VERNAM | 6.00 | none | — | | | | | | | 60 |
|   | VERNAM | 6.00 | 0.50 | PPI | | | | | | | *(20) |
|   | VERNAM | 6.00 | 2.00 | PPI | | | | | | | 60 |
|   | VERNAM | 6.00 | none | — | | | | | | | 60 |
|   | VERNAM | 6.00 | 0.50 | PPI | | | | | | | (60) |
|   | VERNAM | 6.00 | 5.00 | PPI | | | | | | | 60 |
|   | VERNAM | 6.00 | none | — | | | | | | | 55 |
|   | VERNAM | 6.00 | 0.50 | PPI | | | | | | | (55) |
|   | VERNAM | 6.00 | 5.00 | PPI | | | | | | | 55 |
| 2 | VERNAM | 1.25 | none | — | 90 | 100 | 70 | 100 | 75 | | |
|   | VERNAM | 1.25 | 5.00 | IF | *80 | 100 | 70 | 100 | *50 | | |
|   | VERNAM | 6.00 | none | — | | | | | | 90 | 40 |
|   | VERNAM | 6.00 | 5.00 | IF | | | | | | 90 | 40 |
| 3 | VERNAM | 1.25 | none | — | 100 | 100 | 55 | 100 | 100 | | |
|   | VERNAM | 1.25 | 5.00 | IF | *85 | 100 | 75 | *65 | *70 | | |
|   | VERNAM | 6.00 | none | — | | | | | | 90 | 40 |
|   | VERNAM | 6.00 | 5.00 | IF | | | | | | 90 | 100 |
| 4 | VERNAM | 1.25 | none | — | 100 | 100 | 55 | 100 | 100 | | |
|   | VERNAM | 1.25 | 5.00 | IF | 100 | 100 | 70 | 100 | *85 | | |
|   | VERNAM | 6.00 | none | — | | | | | | 90 | 40 |
|   | VERNAM | 6.00 | 5.00 | IF | | | | | | *35 | 100 |
| 5 | VERNAM | 1.25 | none | — | 100 | 100 | 55 | 100 | 100 | | |
|   | VERNAM | 1.25 | 5.00 | IF | *75 | *85 | 70 | 100 | 100 | | |
|   | VERNAM | 6.00 | none | — | | | | | | 90 | 40 |
|   | VERNAM | 6.00 | 5.00 | IF | | | | | | *70 | 40 |
| 6 | VERNAM | 1.25 | none | — | 100 | 100 | 67 | 96 | 92 | | |
|   | VERNAM | 1.25 | 5.00 | IF | *60 | 100 | 65 | 96 | 92 | | |
|   | VERNAM | 6.00 | none | — | | | | | | 90 | 45 |
|   | VERNAM | 6.00 | 5.00 | IF | | | | | | *10 | 100 |
|   | VERNAM | 6.00 | none | — | | | | | | | 60 |
|   | VERNAM | 6.00 | 1.00 | PPI | | | | | | | *45 |
|   | VERNAM | 6.00 | 2.00 | PPI | | | | | | | *50 |
|   | VERNAM | 6.00 | 5.00 | PPI | | | | | | | 60 |
|   | EPTAM | 6.00 | none | — | | | | | | 90 | |
|   | EPTAM | 6.00 | 0.0025 | PPI | | | | | | 90 | |
|   | EPTAM | 6.00 | 0.025 | PPI | | | | | | 90 | |
|   | EPTAM | 6.00 | 0.05 | PPI | | | | | | *(70) | |
|   | EPTAM | 6.00 | none | PPI | | | | | | 80 | |
|   | EPTAM | 6.00 | 0.0125 | PPI | | | | | | 80 | |
|   | EPTAM | 6.00 | 0.025 | PPI | | | | | | 80 | |
|   | EPTAM | 6.00 | 0.05 | PPI | | | | | | (80) | |
|   | EPTAM | 6.00 | none | PPI | | | | | | 75 | |
|   | EPTAM | 6.00 | 0.05 | PPI | | | | | | *(40) | |
|   | EPTAM | 6.00 | 0.05 | PPI | | | | | | *10 | |
|   | EPTAM | 6.00 | 5.00 | PPI | | | | | | *20 | |
| 7 | VERNAM | 1.25 | none | — | 100 | 100 | 55 | 100 | 100 | | |

TABLE IV-continued

| Cmpd. No. | Herbicide | Rate | Antidote Rate | Method | Antidotal Effectiveness |||||||
|---|---|---|---|---|---|---|---|---|---|---|---|
| | | | | | Milo % Inj | Wheat % Inj | Cotton % Inj | Rice % Inj | Barley % Inj | Corn % Inj | Soybean % Injury |
| | VERNAM | 1.25 | 5.00 | IF | 100 | 100 | 55 | *85 | *85 | | |
| | VERNAM | 6.00 | none | — | | | | | | 90 | 40 |
| | VERNAM | 6.00 | 5.00 | IF | | | | | | 90 | 100 |
| 8 | VERNAM | 1.25 | none | — | 95 | 100 | 55 | 100 | 90 | | |
| | VERNAM | 1.25 | 5.00 | IF | 95 | 100 | 65 | 100 | 90 | | |
| | VERNAM | 6.00 | none | — | | | | | | 90 | 50 |
| | VERNAM | 6.00 | 5.00 | IF | | | | | | *55 | 50 |
| 9 | VERNAM | 1.25 | none | — | 90 | 100 | 70 | 100 | 75 | | |
| | VERNAM | 1.25 | 5.00 | IF | 90 | 100 | 70 | 100 | *50 | | |
| | VERNAM | 6.00 | none | — | | | | | | 90 | 40 |
| | VERNAM | 6.00 | 5.00 | IF | | | | | | *80 | 40 |
| 10 | VERNAM | 1.25 | none | — | 100 | 95 | 60 | 97 | 90 | | |
| | VERNAM | 1.25 | 5.00 | IF | 100 | 95 | *35 | 97 | 90 | | |
| | VERNAM | 6.00 | none | — | | | | | | 95 | 65 |
| | VERNAM | 6.00 | 5.00 | IF | | | | | | *85 | 65 |
| | VERNAM | 1.50 | none | IF | | 50 | | | | | |
| | VERNAM | 1.50 | 1.00 | IF | | 50 | | | | | |
| | VERNAM | 1.50 | 5.00 | IF | | *45 | | | | | |
| 11 | VERNAM | 1.25 | none | — | 100 | 95 | 60 | 97 | 90 | | |
| | VERNAM | 1.25 | 5.00 | IF | 100 | 95 | 60 | 97 | 90 | | |
| | VERNAM | 6.00 | none | — | | | | | | 95 | 65 |
| | VERNAM | 6.00 | 5.00 | IF | | | | | | *75 | 90 |
| 12 | VERNAM | 1.25 | none | — | 100 | 100 | 40 | 95 | 90 | | |
| | VERNAM | 1.25 | 5.00 | IF | 100 | 100 | 40 | *80 | 90 | | |
| | VERNAM | 6.00 | none | — | | | | | | 90 | 60 |
| | VERNAM | 6.00 | 5.00 | IF | | | | | | *80 | 100 |
| 13 | VERNAM | 1.25 | none | — | 100 | 100 | 55 | 100 | 100 | | |
| | VERNAM | 1.25 | 5.00 | IF | 100 | 100 | 65 | 100 | *80 | | |
| | VERNAM | 6.00 | none | — | | | | | | 90 | 40 |
| | VERNAM | 6.00 | 5.00 | IF | | | | | | 90 | 100 |
| 14 | VERNAM | 1.25 | none | — | 100 | 95 | 70 | 100 | 95 | | |
| | VERNAM | 1.25 | 5.00 | IF | 100 | 95 | 70 | 100 | 95 | | |
| | VERNAM | 6.00 | none | — | | | | | | 90 | 65 |
| | VERNAM | 6.00 | 5.00 | IF | | | | | | *80 | *40 |
| | VERNAM | 6.00 | none | — | | | | | | | 65 |
| | VERNAM | 6.00 | 1.00 | IF | | | | | | | *30 |
| | VERNAM | 6.00 | 5.00 | IF | | | | | | | *40 |
| | VERNAM | 6.00 | none | — | | | | | | | 65 |
| | VERNAM | 6.00 | 0.50 | PPI | | | | | | | 65 |
| | VERNAM | 6.00 | 2.00 | PPI | | | | | | | *60 |
| | VERNAM | 1.25 | none | — | 100 | 95 | 60 | 97 | 90 | | |
| | VERNAM | 1.25 | 5.00 | IF | 100 | 95 | 60 | 97 | *80 | | |
| | VERNAM | 6.00 | none | — | | | | | | 95 | 65 |
| | VERNAM | 6.00 | 5.00 | IF | | | | | | 95 | 65 |

TABLE V

| Cmpd. No. | Herbicide | Rate | Antidote Rate | Method | Herbicidal Effectiveness |||
|---|---|---|---|---|---|---|---|
| | | | | | Water-grass | Fox-tail | Shatter-cane |
| 1 | VERNAM | 6.00 | none | — | 99 | 99 | |
| | VERNAM | 6.00 | 0.50 | PPI | 99 | 99 | |
| | VERNAM | 6.00 | 2.00 | PPI | 99 | 99 | |
| | VERNAM | 6.00 | none | — | 100 | 100 | |
| | VERNAM | 6.00 | 0.50 | PPI | 100 | 100 | |
| | VERNAM | 6.00 | 2.00 | PPI | 100 | 100 | |
| | VERNAM | 6.00 | none | — | 98 | 100 | |
| | VERNAM | 6.00 | 0.50 | PPI | 98 | 100 | |
| | VERNAM | 6.00 | 2.00 | PPI | 98 | 100 | |
| 6 | VERNAM | 6.00 | none | — | 97 | 97 | |
| | VERNAM | 6.00 | 1.00 | PPI | 97 | 97 | |
| | VERNAM | 6.00 | 2.00 | PPI | 97 | 97 | |
| | VERNAM | 6.00 | 5.00 | PPI | 97 | 97 | |
| | EPTAM | 6.00 | none | — | 100 | 100 | |
| | EPTAM | 6.00 | 0.0025 | PPI | 100 | 100 | |
| | EPTAM | 6.00 | 0.025 | PPI | 100 | 100 | |
| | EPTAM | 6.00 | 0.05 | PPI | 100 | 100 | |
| | EPTAM | 6.00 | none | — | 100 | 100 | |
| | EPTAM | 6.00 | 0.0125 | PPI | 100 | 100 | |
| | EPTAM | 6.00 | 0.025 | PPI | 100 | 100 | |
| | EPTAM | 6.00 | 0.05 | PPI | 100 | 100 | |
| | EPTAM | 6.00 | none | — | 100 | 100 | |
| | EPTAM | 6.00 | 0.05 | PPI | 100 | 100 | |
| | EPTAM | 6.00 | 0.50 | PPI | 100 | 100 | |
| | EPTAM | 6.00 | 5.00 | PPI | 100 | 100 | |
| 10 | VERNAM | 1.50 | none | — | 100 | | 100 |
| | VERNAM | 1.50 | 1.00 | IF | 100 | | 100 |
| | VERNAM | 1.50 | 5.00 | IF | 100 | | 100 |
| 14 | VERNAM | 6.00 | none | — | 98 | 98 | |
| | VERNAM | 6.00 | 1.00 | IF | 98 | 98 | |
| | VERNAM | 6.00 | 5.00 | IF | 98 | 98 | |
| | VERNAM | 6.00 | none | — | 98 | 100 | |
| | VERNAM | 6.00 | 0.50 | PPI | 98 | 100 | |
| | VERNAM | 6.00 | 2.00 | PPI | 98 | 100 | |

Test Results

The compounds of this invention show good antidotal activity for a variety of crops. The composition of thiocarbamate herbicide and antidote compound was particularly effective for the reduction of herbicidal injury to corn crops. Use of the antidote compounds did not result in a reduction of herbicidal injury to weeds.

Formulations

A formulation is the incorporation of a formulant in a form which is directly usable on crops and weeds. As defined herein, a "formulant" is the material which is to be formulated. The formulant may be either an antidote compound alone or an herbicide and antidote composition. The purpose of the formulation is to apply the formulant to the locus where it is desired to establish herbicidal selectivity by a convenient method. The "locus" may include soil, seeds, seedlings and vegetation.

The formulations are commonly dusts, wettable powders, granules, solutions or emulsifiable concentrates.

Dusts are free-flowing powder compositions containing the formulant impregnated on a particulate carrier. The particle size of the carriers is usually in the approximate range of 30 to 50 microns. Examples of suitable carriers are talc, bentonite, diatomaceous earth, and pyrophyllite. The composition generally contains up to 50% of formulant. Anti-caking and anti-static agents may also be added. Dusts may be applied by spraying from boom and hand sprayers on airplanes.

Wettable powders are finely divided compositions comprising a particulate carrier impregnated with the formulant and additionally containing one or more surface active agents. The surface active agent promotes rapid dispersion of the powder in an aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols, in which the alcohol groups are free, omegasubstituted polyethylene glycols of relatively long chain length. A list of surface active agents suitable for use in agriculture formulations can be found in Wade Van Valkenburg, *Pesticide Formulations* (Marcel Dekker, Inc., N.Y., 1973) at pages 79–84.

Granules comprise the formulant impregnated on a particulate inert carrier having a particle size of about 1 to 2 millimeters (mm) in diameter. The granules can be made by spraying a solution of the formulant in a volatile solvent onto the granular carrier. Examples of suitable carriers for the preparation of granules include clay, vermiculite, sawdust, and granular carbon.

Emulsifiable concentrates consist of an oil solution of the formulant plus an emulsifying agent. Prior to use the concentrate is diluted with water to form a suspended emulsion of oil droplets. The emulsifiers used are usually a mixture of anionic and nonionic surfactants. Other additives, such as suspending agents and thickeners, may be included in the emulsifiable concentrate.

When the formulant is an antidote and herbicide composition, the proportion of antidote compound to herbicide compound generally ranges from approximately 0.001 to 30 parts by weight of the antidote compound per weight of the herbicide compound.

Formulations generally contain several additives in addition to the formulant and carrier or agent. Among these are inert ingredients, diluent carriers, organic solvents, water, oil and water, water in oil emulsions, carriers of dusts and granules, and surface active wetting, dispersing and emulsifying agents. Fertilizers, e.g., ammonium nitrate, urea and superphosphate, may be included. Aids to rooting and growth, e.g., compost, manure, humus and sand, may also be included.

Alternatively, the antidote compounds and herbicide and antidote compositions of this invention can be applied to a crop by addition of the formulant to irrigation water supplied to the field to be treated. This method of application permits the penetration of the compositions into the soil as the water is absorbed.

As another alternative, the formulant can be applied to the soil in the form of a solution in a suitable solvent. Solvents frequently used in these formulations include kerosene, fuel oil, xylene, petroleum fractions with boiling ranges above xylene and aromatic petroleum fractions rich in methylated naphthalenes. Liquid solutions, like dusts, may be applied by spraying from boom and hand sprayers on airplanes.

What is claimed is:

1. A herbicidal composition comprising:
(a) an herbicidally effective amount of a compound of the formula

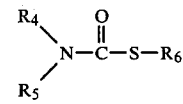

in which
R₄ is alkyl having 1–6 carbon atoms, inclusive;
R₅ is alkyl having 1–6 carbon atoms, inclusive; and
R₆ is alkyl having 1–6 carbon atoms, inclusive; and
(b) an non-phytotoxic antidotally effective amount of a compound of the formula

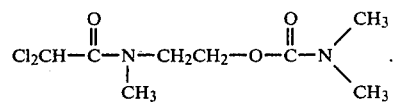

2. A composition according to claim 1 wherein R₄, R₅ and R₆ are all propyl.

3. A composition according to claim 1 wherein R₄ and R₅ are both n-propyl and R₆ is ethyl.

4. A method of controlling undesirable vegetation and reducing herbicidal crop injury due to a thiocarbamate herbicide comprising applying to the locus where control is desired
(a) an herbicidally effective amount of a compound of the formula

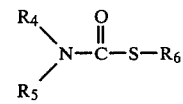

in which
R₄ is alkyl having 1–6 carbon atoms, inclusive;
R₅ is alkyl having 1–6 carbon atoms, inclusive; and
R₆ is alkyl having 1–6 carbon atoms, inclusive; and
(b) a non-phytotoxic antidotally effective amount of a compound of the formula

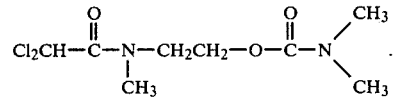

5. A method as defined in claim 4 wherein R₄, R₅ and R₆ are all propyl.

6. A method as defined in claim 4 wherein R₄ and R₅ are both n-propyl and R₆ is ethyl.

* * * * *